United States Patent
Joray et al.

(10) Patent No.: US 11,274,071 B2
(45) Date of Patent: Mar. 15, 2022

(54) SYNTHESIS OF ALKYL 2-ACETYL-5,9,13-TRIMETHYLTETRADECA-4,8,12-TRIENOATES AND DERIVATIVES BY A NON-CONTINUOUS PRODUCTION PROCESS

(71) Applicant: DSM IP ASSETS B.V., Heerlen (NL)

(72) Inventors: Marcel Joray, Kaiseraugst (CH); René Tobias Stemmler, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 16/954,671

(22) PCT Filed: Dec. 11, 2018

(86) PCT No.: PCT/EP2018/084270
§ 371 (c)(1),
(2) Date: Jun. 17, 2020

(87) PCT Pub. No.: WO2019/121134
PCT Pub. Date: Jun. 27, 2019

(65) Prior Publication Data
US 2020/0308090 A1    Oct. 1, 2020

(30) Foreign Application Priority Data
Dec. 20, 2017  (EP) .................... 17208961

(51) Int. Cl.
*C07C 45/65*    (2006.01)
*C07C 67/347*   (2006.01)

(52) U.S. Cl.
CPC ............ *C07C 45/65* (2013.01); *C07C 67/347* (2013.01)

(58) Field of Classification Search
CPC ............................. C07C 45/65; C07C 67/347
See application file for complete search history.

(56) References Cited

U.S. PATENT DOCUMENTS

2017/0044084 A1*  2/2017  Schelwies ............... C07C 45/62

FOREIGN PATENT DOCUMENTS

| CN | 105859534 A | * | 8/2016 |
| EP | 0 044 771 | | 1/1982 |

OTHER PUBLICATIONS

International Search Report for PCT/EP2018/084270 dated Feb. 13, 2019, 3 pages.
Written Opinion of the ISA for PCT/EP2018/084270 dated Feb. 13, 2019, 5 pages.

* cited by examiner

*Primary Examiner* — Yong L Chu
(74) *Attorney, Agent, or Firm* — Nixon & Vanderhye P.C.

(57) ABSTRACT

The present invention relates to the manufacturing of a process of alkyl 2-acetyl-5,9,13-trimethyltetradeca-4,8,12-trienoates and alkyl 2-acetyl-9,13-di-methyl-5-methyl-enetetradeca-8,12-dienoate as well as 6,10,14-trimethyl-penta-deca-5,9,13-trien-2-one and 10,14-dimethyl-6-methylenepentadeca-9,13-dien-2-5 one and 6,10,14-trimethylpentadecan-2-one.

8 Claims, 2 Drawing Sheets

SYNTHESIS OF ALKYL 2-ACETYL-5,9,13-TRIMETHYLTETRADECA-4,8,12-TRIENOATES AND DERIVATIVES BY A NON-CONTINUOUS PRODUCTION PROCESS

CROSS-REFERENCE TO RELATED APPLICATIONS

This application is the U.S. national phase of International Application No. PCT/EP2018/084270 filed Dec. 11, 2018 which designated the U.S. and claims priority to EP Patent Application No. 17208961.7 filed Dec. 20, 2017, the entire contents of each of which are hereby incorporated by reference.

TECHNICAL FIELD

The present invention relates to the manufacturing of alkyl 2-acetyl-5,9,13-trimethyltetradeca-4,8,12-trienoates and alkyl 2-acetyl-9,13-dimethyl-5-methylene-tetradeca-8,12-dienoate as well as 6,10,14-trimethylpentadeca-5,9,13-trien-2-one and 10,14-dimethyl-6-methylenepentadeca-9,13-dien-2-one and 6,10,14-trimethyl-pentadecan-2-one.

BACKGROUND OF THE INVENTION 6,10,14-trimethylpentadecan-2-one (=hexahydrofarnesyl acetone) is a compound which is an important intermediate, or starting material, respectively, for the synthesis of vitamin E.

A known pathway towards 6,10,14-trimethylpentadecan-2-one consists of hydrogenation of 6,10,14-trimethylpentadeca-5,9,13-trien-2-one (=farnesyl acetone) and/or double-bond regioisomers thereof, such as 10,14-dimethyl-6-methylenepentadeca-9,13-dien-2-one.

Several pathways exist for the synthesis of 6,10,14-trimethylpentadeca-5,9,13-trien-2-one. One of these pathways starts from beta-farnesene. Beta-farnesene is a compound which exists in nature. Recent developments in the bio-technological synthesis of beta-farnesene have increased the interest in this route.

CN 105859534 A discloses a continuous process for the synthesis of 6,10,14-trimethylpentadeca-5,9,13-trien-2-one and 10,14-dimethyl-6-methylene-pentadeca-9,13-dien-2-one from beta-farnesene using rhodium complexes and sulfonated triphenylphosphines in a continuous reactor. The reaction time, however, is rather long and very high reaction temperatures are used. It has been observed that the selectivity clearly decreases significantly at higher temperatures which is primarily due to dimerization reactions of beta-farnesene. As a consequence, such a process is only of very limited interest for an industrial and large-scale process.

WO 2015/165959 A1 discloses a discontinuous process under stirring at fully turbulent stirring conditions (Reynolds number $R_e$ of more than 10'000) for the synthesis of 6,10,14-trimethylpentadeca-5,9,13-trien-2-one and -me10,14-dimethyl-6thylenepentadeca-9,13-dien-2-one starting from beta-farnesene using trisodium tris(3-sulfonatophenyl)phosphine (=TPPTS) and a rhodium complex.

EP 0 044 771 A1 discloses as well the use of trisodium tris(3-sulfonato-phenyl)phosphine (=TPPTS) and a rhodium complex for the synthesis of methyl-2-acetyl-9,13-dimethyl-5-methylenetetradeca-8,12-dienoate and methyl-2-acetyl-5,9,13-trimethyltetradeca-4,8,12-trienoate starting from beta-farnesene.

Due to the importance of any cost aspects, industry shows a constant need and interest for improving synthesis of products at an industrial scale.

Therefore, there is a need for a highly cost-efficient synthesis involving possibilities for high volume, low catalyst loadings and reduced reaction times at nevertheless high reaction yields.

SUMMARY OF THE INVENTION

Therefore, the problem to be solved by the present invention is to increase the attractiveness of the synthesis of alkyl 2-acetyl-5,9,13-trimethyltetradeca-4,8,12-trienoates and alkyl 2-acetyl-9,13-dimethyl-5-methylenetetradeca-8,12-dienoate as well as 6,10,14-trimethylpentadeca-5,9,13-trien-2-one and 10,14-di-methyl-6-methylenepentadeca-9,13-dien-2-one and 6,10,14-trimethylpentadecan-2-one from beta-farnesene.

It has been particularly shown that the present invention enables a cost-efficient process. This can particularly be achieved by the use of a non-continuous process on the one hand and the use of water-soluble phosphine salt of mono- or disulfonated triphenylphosphines of formula (IV-a) or (IV-b) on the other hand. It has been surprisingly found that by the use of these water-soluble phosphine salts a significantly faster reaction can be achieved at nevertheless high yield, as compared to the respective trisulfonated triphenylphosphine salts used in the state of the art documents.

Further aspects of the invention are subject of further independent claims. Particularly preferred embodiments are subject of dependent claims.

DETAILED DESCRIPTION OF THE INVENTION

In a first aspect, the present invention relates to a process for manufacturing a compound of formula (I)

by reacting a compound of formula (II) and a compound of formula (III)

in a non-continuous process in the presence of
either
i) a mixture of a rhodium complex and water-soluble phosphine salt of formula (IV-a) or (IV-b)
or
ii) a rhodium complex obtained from a reaction of a rhodium complex and water-soluble phosphine salt of formula (IV-a) or (IV-b)

and in the presence of water and an organic solvent being selected from the group consisting of $C_1$-$C_5$ alcohols, alkylethers of $C_1$-$C_5$ alcohols, $C_2$-$C_6$ alkane diols, monoalkylethers of $C_2$-$C_6$ alkane diols, dialkylethers of $C_2$-$C_6$ alkane diols, esters of $C_1$-$C_5$ carboxyl acids or diacids, lactones and lactames;
wherein
the residue $R^1$ stands for a $C_{1-10}$-alkyl group, preferably for a $C_{1-5}$-alkyl group, more preferably for a methyl group;
n stands for a value of 1-4, preferably for 1;
$M^{n+}$ stands for an organic or inorganic cation of the charge +n, preferably for an alkali metal ion, most preferably for $Na^+$
wherein the dotted line in formula (I) indicates a carbon-carbon double bond which is located at one of the two indicated positions.

For sake of clarity, some terms as used in the present document are defined as follows:

In the present document, a "$C_{x-y}$-alkyl" group is an alkyl group comprising x to y carbon atoms, i.e., for example, a $C_{1-3}$-alkyl group is an alkyl group comprising 1 to 3 carbon atoms. The alkyl group can be linear or branched. For example —CH($CH_3$)—$CH_2$-$CH_3$ is considered as a $C_4$-alkyl group.

A "$C_{x-y}$-alkylene" group is an alkylene group comprising x to y carbon atoms, i.e., for example, a $C_{1-3}$-alkylene group is an alkylene group comprising 1 to 3 carbon atoms. The alkylene group can be linear or branched. For example, —$CH_2$-$CH_2$-$CH_2$— and —CH($CH_3$)—$CH_2$— and —C($CH_2$-$CH_3$)— and —C($CH_3$)$_2$— are all considered as a $C_3$-alkylene group.

In case identical labels for symbols or groups are present in several formulae, in the present document, the definition of said group or symbol made in the context of one specific formula applies also to other formulae which comprises the same said label.

It is key of the invention that the above reaction is a non-continuous process. This means that the process is either performed batchwise or semi-batchwise. In contrast to a continuous process where starting materials are added in a continuous manner, and the product leaves the reaction vessel continuously, a batchwise process comprises the addition of reaction partners in a reactor, and only after the reaction has taken place, the complete reaction mixture is taken out of the reactor. In a semi-batchwise process, one or more reagents are added over time to the reaction vessel, and only after the reaction has taken place, the complete reaction mixture is taken out of the reactor.

The batchwise and semi-batchwise processes have the advantage that large volumes of the compound of formula (I) can be produced cost-efficiently and with standard, economic equipment. As the reaction time is one of the key elements, for the low-cost production of large volumes, it is important that the reaction rate is high. It has been found, that the present process is exactly showing this advantage.

It has been shown that in continuous processes for this reaction, particularly using micro-flow reactors, it is necessary to increase the temperature to increase the conversion. However, by doing so, the selectivity of the reaction, i.e. forming specifically the compound of formula (I) is decreased significantly. As a result of this decrease in selectivity, higher amounts of dimerization products can be found in the reaction product. On contrary to this, the present invention allows the synthesis of compound of formula (I) at very low temperatures with a very high conversion and at the same time with a very high selectivity. Particularly, the amount of dimerization products is minimal.

In the above process, the compound of formula (II) is reacted with the compound of formula (III)

The compound of formula (II), also known as beta-farnesene, is a naturally occurring compound and is commercially available.

The compound of formula (III) is a beta-keto ester. Suitable beta-keto esters can be synthesized by methods known to the person skilled in the art and are also commercially available.

The compound of formula (II) is reacted with the compound of formula (III) in a non-continuous process in the presence of
either
i) a mixture of a rhodium complex and water-soluble phosphine salt of formula (IV-a) or (IV-b)

or ii) a rhodium complex obtained from a reaction of a rhodium complex and water-soluble phosphine salt of formula (IV-a) or (IV-b)

and and in the presence of water and an organic solvent being selected from the group consisting of $C_1$-$C_5$ alcohols, alkylethers of $C_1$-$C_5$ alcohols, $C_2$-$C_6$ alkane diols, monoalkylethers of $C_2$-$C_6$ alkane diols, dialkylethers of $C_2$-$C_6$ alkane diols, esters of $C_1$-$C_5$ carboxyl acids or diacids, lactones and lactames.

For this reaction, a rhodium complex is necessary. This rhodium complex can be formed either in situ (see variant i) above) or prepared beforehand and added as such (see variant ii) above).

Details of the rhodium complex and the water-soluble phosphine salt of formula (IV-a) or (IV-b) and its synthesis are known from EP 0 044 771 A1, EP 0 441 708 A1 and U.S. Pat. No. 4,621,165.

The preferred rhodium complex is a rhodium (I) complex coordinating two alkenes or a diene, particularly cycloocta-1,5-diene or norbornadiene, as ligand.

It has been shown, that the rhodium complex [Rh(COD)X]$_2$ is particularly suitable for the purpose of the invention, wherein COD stands for cycloocta-1,5-diene and X is a halide, preferably Cl. The most preferred rhodium complex is [Rh(COD)Cl]$_2$.

The water-soluble phosphine salt of formula (IV-a) or (IV-b) can be synthesized according to the method given in EP 0 107 006 A1.

The water-soluble phosphine salt of formula (IV-a) is (m-sulfonatophenyl)-diphenylphosphine salt and the water-soluble phosphine salt of formula (IV-b) is bis(m-sulfonatophenyl)phenylphosphine salt. Therefore, this phospine salt has one or two sulfonato ($SO_3^-$) groups. In other words, not all of the tree phenyl rings of triphenylphosphine are sulfonated, as it is in the case for example in tris(3-sulfophenyl)phosphine trisodium salt (=trisodium tris(3-sulfonatophenyl)-phosphine=TPPTS), as known in the state of the art documents.

$M^{n+}$ stands for an organic or inorganic cation of the charge +n, preferably for an alkali metal ion, most preferably for Na$^+$.

Therefore, preferred water-soluble phosphine salt of formula (IV-a) is sodium (m-sulfonatophenyl)diphenylphosphine (=sodium triphenylphosphine-monosulfonate=TPPMS) and the preferred water-soluble phosphine salt of formula (IV-b) is disodium bis(3-sulfonatophenyl)phenylphosphine (=disodium triphenylphosphinedisulfonate=TPPDS).

We have found that the compound of formula (IV-a), particularly TPPMS, and of formula (IV-b), particularly TPPDS, show a significant faster reaction compared to the respective water-soluble trisulfonated phosphine salt (such as TPPTS). Nevertheless, the high yield and selectivity is maintained. It has been shown that these advantages are particularly pronounced when the water-soluble phosphine salt of formula (IV-a), preferably TPPMS, is used.

Hence, compound of formula (IV-a), preferably TPPMS, is the preferred water-soluble phosphine salt within this invention.

The above reaction of a compound of formula (II) and a compound of formula (III) performed in the presence of water and an organic solvent being selected from the group consisting of $C_1$-$C_5$ alcohols, alkylethers of $C_1$-$C_5$ alcohols, $C_2$-$C_6$ alkane diols, monoalkylethers of $C_2$-$C_6$ alkane diols, dialkylethers of $C_2$-$C_6$ alkane diols, esters of $C_1$-$C_5$ carboxyl acids or diacids, lactones and lactames.

Particular suitable as $C_2$-$C_6$ alkane diols are ethylene glycol, propylene glycols, polyethylene glycols (PEG), such as PEG-200 or PEG-600, and poly propylene glycols (PPG).

Particular suitable as monoalkylethers of $C_2$-$C_6$ alkane diols, particularly mono-$C_1$-$C_4$ alkylethers of ethylene glycol, propylene glycols, polyethylene glycols (PEG), such as PEG-200 or PEG-600, and poly propylene glycols (PPG).

Particular suitable as dialkylethers of $C_2$-$C_6$ alkane diols, particularly di-$C_1$-$C_4$ alkylethers of ethylene glycol, propylene glycols, polyethylene glycols (PEG), such as PEG-200 or PEG-600, and poly propylene glycols (PPG).

It is preferred that the molar ratio of rhodium complex and water-soluble phosphine salt of formula (IV-a) or (IV-b) is 3-50, preferably 5-40, more preferably 10-25.

It is further preferred that the molar ratio of the compound of formula (III) to the compound of formula (II) is 1-5, preferably 1.2-3, most preferably 1.7-2.5.

The molar ratio of the rhodium complex is preferably used in a concentration of between 0.01-0.5 mol-%, preferably 0.01-0.05 mol-%, with respect to the amount of the compound of formula (II).

The reaction of the compound of formula (II) and a compound of formula (III) is preferably carried out in the presence of water and an alcohol, particularly ethanol, in a volume ratio of water to alcohol of 5:1-1:10, particularly 2:1-1:4, preferably 1.5:1-1:2.

The above process yields compound of formula (I).

The dotted line in formula (I) indicates a carbon-carbon double bond which is located at one of the two indicated positions

In other words, the formula of this compound (I), shown above, is a schematic representation of the following two formulae (I-a) and (I-b)

Typically, the process of manufacturing yields a mixture of the compounds of formula (I-a) and (I-b). A separation of such a mixture into the individual isomers of formula (I-a) and (I-b) is generally possible by using suitable separation techniques, but very difficult to achieve. However, considering that the compound of formula (I) can be transformed to a compound of formula (V) which then is preferably hydrogenated in a step d) to compound of formula (VI), as described later on in this document, an isolation of the two isomers, i.e. formula (I-a) and (I-b), is not necessary as the carbon-carbon double bond at issue is hydrogenated and both isomers yield the same product upon hydrogenation, i.e. the compound of formula (VI)

In a further aspect, the present invention relates to a process for manufacturing a compound of formula (V)

comprising the steps
 a) manufacturing a compound of formula (I) according to a process as it has been described above in great detail;
 b) decarboxylation of the compound of formula (I) obtained in step a) in the presence of water to yield a compound of formula (V).

The compound of formula (I) can be isolated after step a) or it can be directly transformed to the compound of formula (V) by step b).

The decarboxylation step b) can be carried out with or without a base.

If the decarboxylation step b) is performed in the presence of a base, suitable bases are particularly alkali metal and alkaline earth metal hydroxides, alkali metal and alkaline earth metal hydrogencarbonates, alkali metal and alkaline earth metal carbonates, alkali metal phosphates or alkali metal alkanolates of $C_1$-$C_6$-alkanols. Preference is given to using alkali metal hydroxides such as sodium hydroxide or potassium hydroxide, alkali metal carbonates such as sodium carbonate or potassium carbonate, alkali metal hydrogencarbonates such as sodium hydrogencarbonate or potassium hydrogencarbonate, alkali metal phosphates such as $Na_3PO_4$ or $K_3PO_4$ or alkali metal alkanolates such as sodium methoxide, sodium ethoxide, sodium propoxide, sodium butoxide, potassium methoxide, potassium ethoxide or potassium butoxide as base.

Particular preference is given to using sodium carbonate, potassium carbonate and sodium phosphate. Very particular preference is given to using sodium carbonate.

In a specific embodiment, step b) is carried out in the presence of sodium carbonate.

In a further aspect, the present invention relates to a process for manufacturing a compound of formula (VI)

comprising the steps
 c) manufacturing a compound of formula (V) according to a process as it has been described above in great detail;
 d) hydrogenating the compound of formula (VI) obtained in step c) to yield a compound of formula (VI).

In other words, the above process comprises the steps
 a) manufacturing a compound of formula (I) according to a process as it has been described above in great detail;
 b) decarboxylation of the compound of formula (I) obtained in step a) in the presence of water to yield a compound of formula (V) and
 d) hydrogenating the compound of formula (VI) obtained in step c) to yield a compound of formula (VI).

The step d) of hydrogenating the compound of formula (VI) to the compound of formula (VI) is typically performed by a reaction with molecular hydrogen in the presence of a hydrogenation catalyst. The hydrogenation catalyst is preferably a noble metal catalyst.

Suitable hydrogenation catalysts are supported palladium catalysts. Suitable supports include many materials, for example aluminium oxide, ceramic support materials or carbon or graphite. Support materials for these catalysts are known to those skilled in the art and are generally used in finely divided form, which can optionally be pressed to give pellets. Particular preference is given to using carbon, in particular activated carbon, as support material. Preference is likewise given to using aluminium oxide as support material. Very particular preference is given to using palladium on carbon.

Particularly preferred is a hydrogenation catalyst selected from the group consisting of palladium on carbon, palladium on silica ($SiO_2$), palladium on $TiO_2$ and palladium on aluminum oxide ($Al_2O_3$).

The hydrogenation in step d) is preferably carried out under pressure, particularly under a pressure of between 1 and 20 bar, more preferably between 1 and 6 bar.

Said reaction provides the desired compound, i. e. the compound of formula (VI), in good yield, conversion and selectivity. The compound of formula (VI) can be isolated and purified, if necessary, from the reaction mixture after the hydrogenation step d) by means of extraction, chromatography, distillation and other techniques known to person skilled in the art.

This reaction is advantageously performed according to the methods as described in the Rhône-Poulenc patents U.S. Pat. Nos. 4,460,786 and 4,621,165, the entire content of which is hereby incorporated by reference.

EXAMPLES

The present invention is further illustrated by the following experiments.

Synthesis of Compound of Formula (I-Me) in a Non-Continuous Process (I-Me)

A 350 mL 4-necked flask equipped with argon inlet, magnetic stirrer, oil bath and thermometer was charged with the respective molar amount of sodium (m-sulfonatophenyl) diphenylphosphine (=sodium triphenylphosphine-monosulfonate=TPPMS), or disodium bis(3-sulfonatophenyl)phenylphosphine (=disodium triphenylphosphinedisulfonate=TPPDS) or tris(3-sulfophenyl)phosphine trisodium salt (=trisodium tris (3-sulfonatophenyl)phosphine=TPPTS) (for comparison) as given in table 1 which was dissolved in the solvent system (20 mL) as indicated in table 1 under an argon atmosphere. Then the respective amount of chloro(1,5-cyclooctadiene)rhodium(I) dimer as indicated in table 1 and sodium carbonate (0.3 mol %) were added forming a homogeneous yellow-orange solution. Subsequently, methyl acetoacetate (MAA) (2.5 equivalents relative to BFN) and trans-β-farnesene (BFN, 48.2 mmol, d=0.83 g/mL, 98.2% by GC, 1.0 equiv.) were added. The two-phase reaction mixture was stirred and heated to reflux (77-87° C. internal temperature, depending on the solvent system; e.g. Ref. 6 (water only) the internal temperature was kept at 80° C.) for the time indicated in table 1. The mixture was then cooled to 23° C.

For the water-free examples of table 1 (Ref.4, Ref.5, Ref.7) in hexane (80 mL) and water 20 mL) were added, the upper hexane phase was separated, and the aqueous phase was extracted with hexane (40 mL). The combined upper, unipolar phases were concentrated in vacuo (40° C., 150 to 40 mbar), furnishing crude compound of formula (I-Me). The conversion, selectivity and yield are indicated in table 1.

For all the other examples of table 1 hexane (50 mL) was added. After 2 minutes of stirring, phases were separated, and the lower, polar H$_2$O/alcohol phase was extracted with hexane (25 mL). The combined upper, nonpolar phases were concentrated in vacuo (40° C., 150 to 40 mbar), furnishing crude compound of formula (I-Me). The conversion, selectivity and yield are indicated in table 1.

The identity of the compound of formula (I-Me) (mixtures of both isomers (see dotted lines)) has been verified by $^1$H NMR and $^{13}$C NMR spectroscopy:

$^1$H NMR (mixture of isomers, ratio ~55:45, 300 MHz, CHLOROFORM-d) δ 1.51 (br s, 1.3 H), 1.52 (br s, 4.7 H), 1.56 (s, 1.3 H), 1.60 (d, J=1.3 Hz, 3 H), 1.85-2.09 (m, 9.1 H), 2.14 (s, 1.3 H), 2.15 (s, 1.7 H), 2.48 (t, J=7.4 Hz, 0.9 H), 3.38 (m, 1 H), 3.64 (s, 1 H), 3.64, (s, 1.3 H), 3.66 (s, 1.7 H), 4.66 (br s, 0.55 H), 4.70 (br s, 0.55 H), 4.93-5.07 (m, 2.45 H) ppm.

$^{13}$C NMR (mixture of isomers ratio ~55:45, 75 MHz, CHLOROFORM-d) δ 15.86, 15.89, 15.95, 17.55, 25.55, 26.03, 26.09, 26.37, 26.59, 26.64, 26.85, 28.88, 29.03, 33.54, 35.57, 39.57, 39.59, 52.14, 52.20, 58.72, 59.46, 110.19, 119.51, 123.67, 123.74, 124.22, 131.09, 135.03, 135.20, 138.40, 147.73, 169.88, 170.07, 202.72, 202.74 ppm.

TABLE 1

Reaction details and results.

| | Phosphine salt | PS/BFN[1] [mol %] | Rh/BFN[2] [mol %] | Solvent system | v/v[3] | rt[4] [h] | conv.[5] [%] | sel.[6] [%] | yield[7] [%] |
|---|---|---|---|---|---|---|---|---|---|
| Ref. 1 | TPPTS | 2 | 0.1 | EtOH/H$_2$O | 1:1 | 1.5 | 6.8 | n.d. | n.d. |
| Ref. 2 | TPPTS | 2 | 0.1 | EtOH/H$_2$O | 1:1 | 7.5 | 24.4 | n.d. | n.d. |
| Ref. 3 | TPPTS | 2 | 0.1 | EtOH/H$_2$O | 1:1 | 24 | 75.1 | n.d. | n.d. |
| 1 | TPPMS | 2 | 0.1 | EtOH/H$_2$O | 1:1 | 1.5 | 30.6 | n.d. | n.d. |
| 2 | TPPMS | 2 | 0.1 | EtOH/H$_2$O | 1:1 | 3 | 49.9 | n.d. | n.d. |
| 3 | TPPMS | 2 | 0.1 | EtOH/H$_2$O | 1:1 | 5 | 78.1 | n.d. | n.d. |
| 4 | TPPMS | 2 | 0.1 | EtOH/H$_2$O | 1:1 | 8 | 97.9 | 94.2 | 92.2 |
| 5 | TPPDS | 1 | 0.05 | EtOH/H$_2$O | 1:1 | 23 | 99.6 | 98.0 | 97.7 |
| 6 | TPPMS | 1 | 0.05 | EtOH/H$_2$O | 1:1 | 23 | 100.0 | 95.5 | 95.5 |
| 7 | TPPMS | 1 | 0.05 | MeOH/H$_2$O | 1:1 | 24 | 99.2 | 95.4 | 94.6 |
| 8 | TPPMS | 1 | 0.05 | EtOH/H$_2$O | 1:1 | 24 | 100.0 | 95.5 | 95.5 |
| 9 | TPPMS | 1 | 0.05 | i-PrOH/H$_2$O | 1:1 | 24 | 99.9 | 92.1 | 92.0 |
| 10 | TPPMS | 1 | 0.05 | 1-BuOH/H$_2$O | 1:1 | 24 | 99.9 | 93.6 | 93.5 |
| Ref. 4 | TPPMS | 1 | 0.05 | MeOH/hexane | 1:1 | 24 | 24.3 | n.d. | n.d. |
| Ref. 5 | TPPMS | 1 | 0.05 | MeOH | — | 24 | 87.1 | 63.1 | 55.0 |
| Ref. 6 | TPPMS | 1 | 0.05 | H$_2$O | — | 24 | 88.2 | 93.4 | 82.4 |
| 11 | TPPMS | 1 | 0.05 | MeOH/H$_2$O | 1:1 | 6 | 92.2 | n.d. | n.d. |
| Ref. 7 | TPPMS | 1 | 0.05 | MeOH | — | 8 | 69.4 | n.d. | n.d. |

TABLE 1-continued

Reaction details and results.

| | Phosphine salt | PS/BFN[1] [mol %] | Rh/BFN[2] [mol %] | Solvent system | v/v[3] | rt[4] [h] | conv.[5] [%] | sel.[6] [%] | yield[7] [%] |
|---|---|---|---|---|---|---|---|---|---|
| Ref. 8 | TPPMS | 1 | 0.05 | H$_2$O | — | 5 | 48.3 | n.d. | n.d. |
| 12 | TPPMS | 1 | 0.05 | MeOH/H$_2$O | 1:1 | 6 | 18.4 | n.d. | n.d. |
| 13 | TPPMS | 1 | 0.05 | MeOH/H$_2$O | 10:1 | 6 | 10.0 | n.d. | n.d. |

[1]PS/BFN = molar ratio of phosphine salt to trans-β-farnesene (in mol-%)
[2]Rh/BFN = molar ratio of [Rh(COD)Cl]$_2$ to trans-β-farnesene (in mol-%)
[3]v/v = volume ratio of solvent A to solvent B in the solvent system A/B
[4]rt = reaction time (in hours)
[5]conv. = conversion of BFN (determined as relative area % by GC (gas chromatography)
[6]sel. = selectivity in formation of compound of formula (I Me) (by GC)
[7]yield is reported as sum of compound of formula (I Me) and (V) and was determined by qNMR.
n.d. = not determined.

Figure 1:
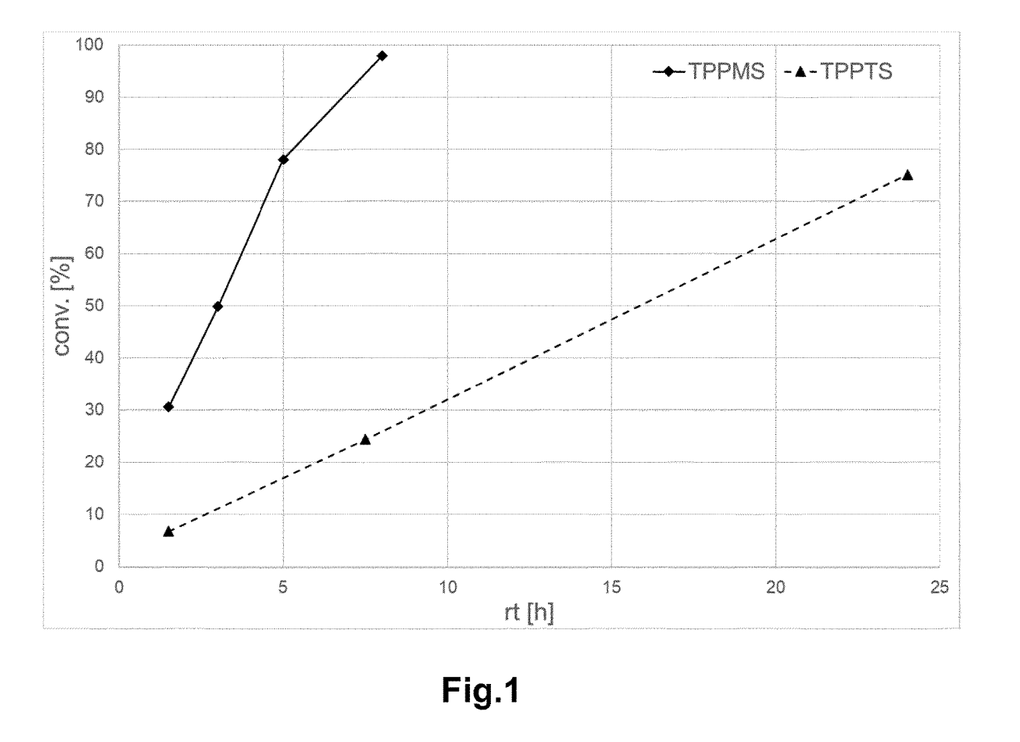
FIG. 1 is a graph of the conversion (%) versus reaction time (h) for a non-continuous reaction for TPPMS and TPPTS in accordance with the data of Table 1 below.

The comparison of results of table 1 of Ref.1-Ref.3 and 1-4 show that the reaction using TPPMS is remarkably faster (higher conversion) than when using TPPTS. This can be also visualized by FIG. 1. Examples 5 and 6 show that TPPMS and TPPDS are so efficient that even with half of the concentration in the phosphine salt the reaction shows a higher conversion after 23 hours as compared with TPPTS (Ref.3). The reaction occurs at very high selectivity. Examples 7-10 show that mixtures of water with different alcohols (methanol, ethanol, iso-propanol are 1-butanol) result in similar fast reactions (and high conversion). When alcohol is used in combination with another solvent (Ref.4) or only alcohol (Ref.5) or water (Ref.6) alone is used the reaction is significantly slower (lower conversion) and less selective towards the desired products.

Comparison of the results of example 11 with Ref.7 and Ref.8 show that if are either alcohol or water are used alone, the reaction is significantly slower. Finally, the comparison of example 12 and 13 show that a volume ratio of alcohol/water=1:1 has faster conversion than a respective volume ratio of 10:1.

Synthesis of Compound of Formula (V)

A 500 mL flask equipped with argon inlet, magnetic stirrer, oil bath, short-path Liebig condenser and thermometer was charged with crude compound of formula (I-Me) (as synthesized above) (271.8 g, 670 mmol, ~79.0 wt. % purity by qNMR, containing some MAA). MAA was distilled off the mixture over 6 h at 85° C. (oil bath temperature) and 15 to 1 mbar. The distillation residue consisted of 234 g concentrated crude compound of formula (I-Me) as colorless oil (660 mmol, 90.4 wt. % by qNMR, 98.5% yield).

A 500 mL 4-necked round-bottom flask equipped with argon inlet, magnetic stirrer, oil bath, thermometer syringe pump, septum and Dean-Stark trap was charged with 229 g of this concentrated crude crude compound of formula (I-Me) (646 mmol) and heated to 180° C. internal temperature (190° C. oil bath). Subsequently, deionized water (18.1 mL, 1.01 mol, 1.56 equiv.) was dosed with a syringe pump below the substrate surface over 6.5 h. The reaction progress was monitored by GC. One hour after complete addition, the reaction was cooled to room temperature. The reaction mixture was transferred into a separation funnel and diluted with hexanes (50 mL). The mixture was extracted with deionized water (2× 100 mL). The combined water phases were extracted with hexanes (50 mL). The combined organic phases were then dried over Na$_2$SO$_4$ and concentrated in vacuo (45° C./200 to 40 mbar), furnishing crude compound of formula (V) as clear pale yellow oil [184.9 g, 641 mmol, 91.0% purity by qNMR as sum of isomers, 97.8% yield from compound of formula (I-Me). The identity of the compound of formula (V) (mixture of both isomers (see dotted lines)) has been verified by $^1$H NMR:

$^1$H NMR (mixture of isomers, ratio ~56:44, 300 MHz, CHLOROFORM-d) δ 1.60 (br s, 6 H), superimposed by 1.57-1.63 (m, 1 H), 1.68 (br d, J=1.3 Hz, 3 H), superimposed by 1.67-1.79 (m, 1.2 H), 1.91-2.14 (m, 10 H), superimposed by 2.13 (s, 3 H), 2.19-2.32 (m, 0.9 H), 2.43 (t, J=7.4 Hz, 1.4 H), 4.69-4.77 (m, 1.1 H), 5.03-5.21 (m, 2.4 H) ppm.

Synthesis of Compound of Formula (VI)

A 1 L steel autoclave was charged with compound of formula (V) (150 g, 89.5% by qNMR, 512 mmol) and dissolved in heptane (150 g). Pd catalyst (5% on charcoal, 1.0 g, 0.47 mmol, 0.1 mol %) was added. After inertization the stirred suspension was heated to 60° C. at ambient pressure. Subsequently, the reaction was started by pressurizing to 10 bar H$_2$. After 10 h the reaction mixture was cooled to room temperature. The reaction mixture was filtered, and the filter washed with little heptane. The filtrate was concentrated in vacuo, furnishing crude 6,10,14-trimethylpentadecan-2-one (compound of formula (VI) (151.9 g).

146.8 g of the crude 6,10,14-trimethylpentadecan-2-one was purified using a distillation apparatus equipped with Vigreux column (15 cm). The main fraction was collected at 108° C./0.26 mbar (vacuum measured at pump), resulting in purified 6,10,14-trimethylpentadecan-2-one (129.4 g, 98.4% by qNMR, 474 mmol, 96% yield). The identity of the compound of formula (VI) has been verified by $^1$H NMR:

$^1$H NMR (300 MHz, CHLOROFORM-d) δ 0.84 (d, J=7.4 Hz, 3 H), superimposed by 0.86 (d, J=6.6 Hz, 3 H), superimposed by 0.87 (d, J=6.8 Hz, 6 H), 0.98-1.68 (m, 19 H), 2.14 (s, 3 H), 2.40 (t, J=7.5 Hz, 2 H) ppm.

Synthesis of Compound of Formula (I-Me) in a Continuous Process (Comparison)

In a further series of experiments the reaction using TPPTS respectively TPPMS as water soluble phosphine salt has been used in a micro-flow reactor.

A Syrris Asia microreactor setup was used to carry out reactions in flow using 250 μL and 1000 μL flow cells, respectively. Two input streams were applied: β-farnesene (neat) and a solution of [Rh(cod)Cl]$_2$, phosphine ligand, methyl acetoacetate and sodium carbonate in a mixture of MeOH/water.

TPPTS

In the first series of continuous reaction experiments, the reaction was performed at different temperatures and residence time (as indicated in table 2) using TPPTS as phosphine salt:

Conditions used: Syrris Asia 250 μL flow cell, MeOH/water 1:5 (v/v, 40 mL), 15 bar, MAA/BFN molar ratio=2.3, [Rh(cod)Cl]$_2$ (0.4 mol %), TPPTS/Rh ratio 20:1, Na$_2$CO$_3$ (0.25 mol %).

TABLE 2

Reaction details in a microreactor using TPPTS as phosphine salt.

| | Temperature [° C.] | Residence time [min] | conv.[5][%] | sel.[6][%] | yield[7][%] |
|---|---|---|---|---|---|
| Ref. 9 | 90 | 13 | 3.1 | 0.4 | 0.4 |
| Ref. 10 | 110 | 13 | 9.8 | 5.5 | 5.5 |
| Ref. 11 | 130 | 13 | 21.9 | 14.7 | 14.7 |

[5]conv. = conversion of BFN (determined as area % by GC (gas chromatography)
[6]sel. = selectivity in formation of compound of formula (I-Me) (by GC)
[7]yield is reported as sum of compound of formula (I-Me) and (V) and was determined by GC-area %.

TPPMS

In the second series of continuous reaction experiments, the reaction was performed at different temperatures and residence times (as indicated in table 3) using TPPMS as phosphine salt:

Conditions used: Syrris Asia 1000 μL flow cell, MeOH/water 7.5:2.5 (v/v, 40 mL), 19 bar, MAA/BFN molar ratio=1.7, [Rh(cod)Cl]$_2$ (0.6 mol %), TPPMS/Rh ratio 10:1, Na$_2$CO$_3$ (1 mol %).

TABLE 3

Reaction details in a microreactor using TPPMS as phosphine salt.

| | Temperature [° C.] | Residence time [min] | conv.[5][%] | sel.[6][%] |
|---|---|---|---|---|
| Ref. 12 | 90 | 7 | 5.3 | 97.1 |
| Ref. 13 | 90 | 13 | 16.0 | 96.8 |
| Ref. 14 | 90 | 20 | 20.0 | 96.3 |
| Ref. 15 | 110 | 3 | 18.1 | 95.5 |
| Ref. 16 | 110 | 7 | 44.3 | 93.5 |
| Ref. 17 | 110 | 13 | 88.3 | 88.4 |
| Ref. 18 | 110 | 20 | 96.3 | 88.6 |
| Ref. 19 | 140 | 3 | 46.1 | 90.6 |
| Ref. 20 | 140 | 7 | 91.9 | 82.3 |
| Ref. 21 | 140 | 13 | 99.0 | 75.6 |
| Ref. 22 | 180 | 0 | 0.0 | 100 |
| Ref. 23 | 180 | 3 | 59.4 | 76.4 |
| Ref. 24 | 180 | 7 | 80.3 | 66.5 |
| Ref. 25 | 180 | 13 | 88.8 | 65.4 |

[5]conv. = conversion of BFN (determined as relative area % by GC (gas chromatography)
[6]sel. = selectivity in formation of compound of formula (I-Me) (by GC)

Figure 2:
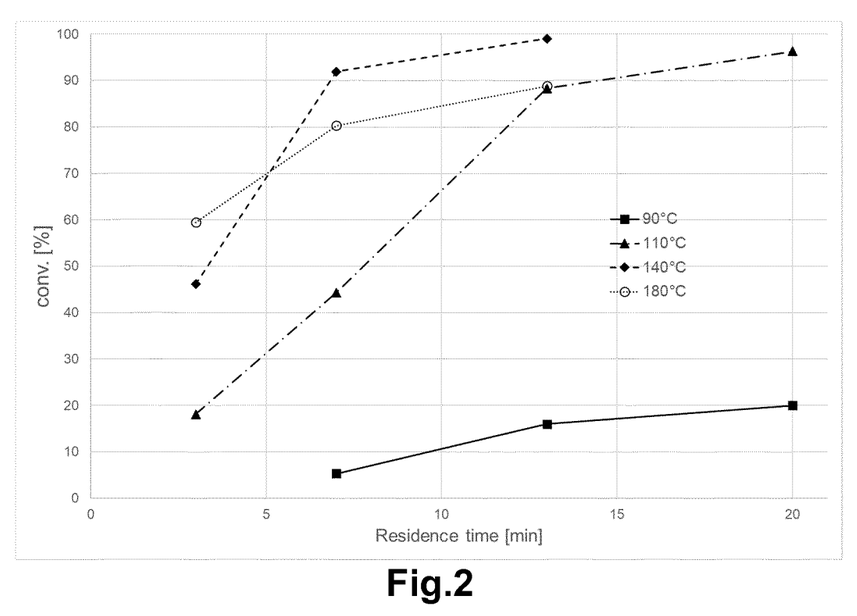
FIGS. 2 and 3 are graphs of the conversion (%) versus reaction time (h) as a function of reaction temperature for a continuous reaction in accordance with the data of Tables 2 and 3 below, respectively.
Figure 3:
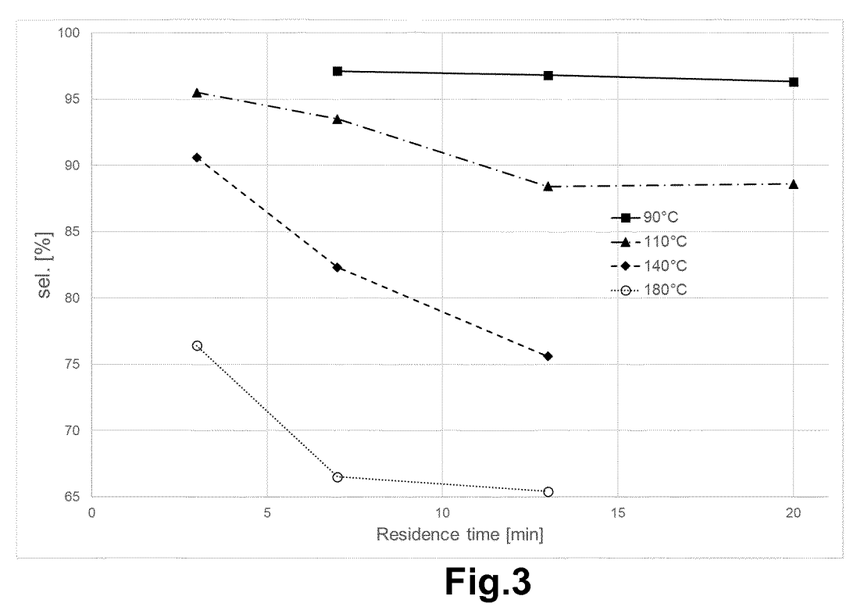

The results in table 2 and 3 show that in a continuous reaction either high conversion and low selectivity or low conversion and high selectivity can be achieved, as visualized in FIGS. 2 and 3.

Comparing with the data from table 1, it is obvious that with the non-continuous process both conversions of higher than 90%, even higher than 95%, and selectivities of higher than 90%, even higher than 92%, particularly higher than 95%, can be easily achieved.

Furthermore, the data of tables 2 and 3 also show that also for the reaction in a continuous process the water-soluble phosphine salt TPPMS is advantageous over TPPTS.

The invention claimed is:
1. A process for manufacturing a compound of formula (I):

wherein the dotted line in formula (I) indicates a carbon-carbon double bond which is located at one of the two indicated positions, wherein the process comprises reacting at temperature of 77° C. to 87° C. a compound of formula (II) and a compound of formula (III):

in a non-continuous process in the presence of either:
i) a mixture of a rhodium complex and water-soluble phosphine salt of formula (IV-a) or (IV-b), or
ii) a rhodium complex obtained from a reaction of a rhodium complex and water-soluble phosphine salt of formula (IV-a) or (IV-b):

and in the presence of water and an organic solvent selected from the group consisting of C$_1$-C$_5$ alcohols, alkylethers of C$_1$-C$_5$ alcohols, C$_2$-C$_6$ alkane diols, monoalkylethers of C$_2$-C$_6$ alkane diols, dialkylethers of C$_2$-C$_6$ alkane diols, esters of C$_1$-C$_6$ carboxyl acids or diacids, lactones and lactames; wherein R$^1$ is a C$_{1-10}$-alkyl group, n is an integer of 1-4, and M$^{n+}$ is an organic or inorganic cation having a charge +n, and wherein
the process achieves conversions and selectivities of the compound of formula (I) of higher than 90%.

2. The process according to claim 1, wherein the water-soluble phosphine salt is of formula (IV-a).

3. The process according to claim 1, wherein the rhodium complex is a rhodium (I) complex coordinating two alkenes or a diene as ligand.

4. The process according to claim 1, wherein the rhodium complex is [Rh(COD)X]$_2$ wherein COD stands for cycloocta-1,5-diene and X is a halide.

5. The process according to claim 1, wherein the rhodium complex and water-soluble phosphine salt of formula (IV-a) or (IV-b) are present in a molar ratio of the rhodium complex to the water-soluble phosphine salt of formula (IV-a) or (IV-b) which is 3-50.

6. The process according to claim 1, wherein the compound of formula (III) and the compound of formula (II) are present in a molar ratio of the compound of formula (III) to the compound of formula (II) which is 1-5.

7. The process according to claim 1, wherein the rhodium complex and the compound of formula (II) are present in molar amounts such that the molar amount of the rhodium complex is between 0.01-0.5 mol-%, with respect to the molar amount of the compound of formula (II).

8. The process according to claim 1, wherein the step of reacting the compound of formula (II) and the compound of formula (III) is performed in the presence of water and an alcohol in a volume ratio of the water to the alcohol of 5:1-1:10.

* * * * *